United States Patent [19]
Conway

[11] Patent Number: 5,370,627
[45] Date of Patent: Dec. 6, 1994

[54] CATHETER SECURING BRIDGE

[76] Inventor: David P. Conway, 7379 Griffith La., Moorpark, Calif. 93021

[21] Appl. No.: 222,380

[22] Filed: Apr. 4, 1994

[51] Int. Cl.⁵ .................................................. A61M 25/02
[52] U.S. Cl. ............................. 604/180; 128/DIG. 26
[58] Field of Search ............... 604/180, 174, 177, 178, 604/179; 128/DIG. 26

[56] References Cited

U.S. PATENT DOCUMENTS

| | | | |
|---|---|---|---|
| 4,333,468 | 6/1982 | Geist | 128/DIG. 26 |
| 4,519,793 | 5/1985 | Galindo | 604/180 |
| 4,614,183 | 9/1986 | McCracken et al. | 604/180 |
| 4,633,863 | 1/1987 | Filips et al. | 604/180 |
| 4,678,462 | 7/1987 | Vaillancourt | 128/DIG. 26 |
| 4,738,662 | 4/1988 | Kalt et al. | 128/DIG. 26 |
| 4,767,411 | 8/1988 | Edmunds | 604/180 |
| 4,822,342 | 4/1989 | Brawner | 604/180 |
| 4,941,882 | 7/1990 | Ward et al. | 604/180 |
| 4,969,880 | 11/1990 | Zamierowski | 604/180 |
| 4,976,700 | 12/1990 | Tollini | 604/180 |
| 5,000,741 | 3/1991 | Kalt | 128/DIG. 26 |
| 5,232,453 | 8/1993 | Plass et al. | 128/DIG. 26 |

*Primary Examiner*—Paul J. Hirsch
*Attorney, Agent, or Firm*—Jack C. Munro

[57] ABSTRACT

A securing bridge for a catheter which is to be inserted into the umbilical stump of a neonate. The bridge is for the purpose of tightly securing in position the portion of the catheter extending from the umbilical stump. The bridge includes a base which is adhesively secured to the skin around the umbilical stump. Mounted on the base are a pair of pivotal flaps which are to be adhesively secured together clamping a portion of the catheter therebetween.

4 Claims, 1 Drawing Sheet

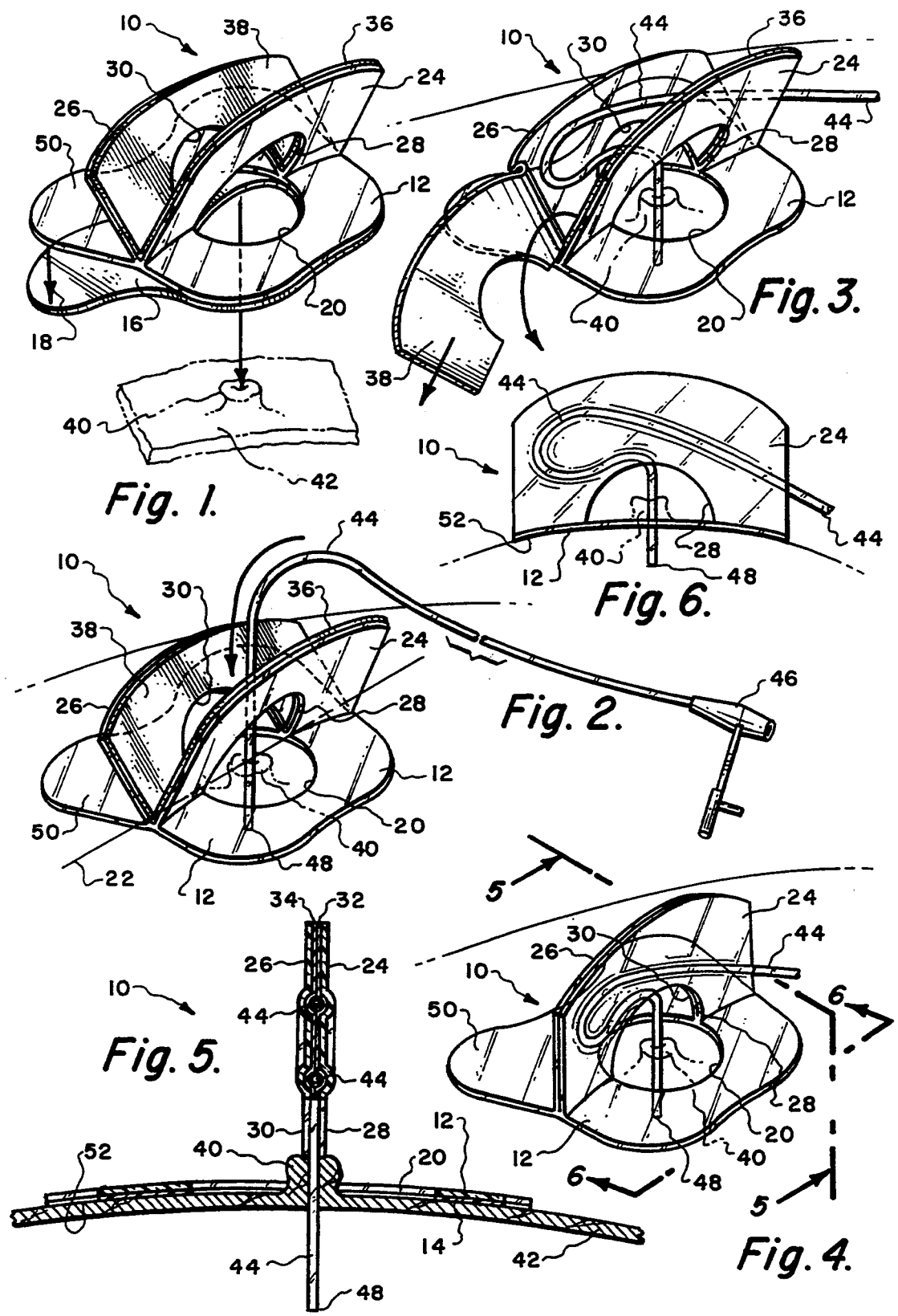

CATHETER SECURING BRIDGE

BACKGROUND OF THE INVENTION

1. Field of the Invention

The field of this invention relates to medical devices and more particularly to a securing bridge for a catheter which has been inserted in the body of a neonate.

2. Description of the Prior Art

Premature human babies frequently require to be given medicine within the bloodstream on a regular basis. It is also normal to have to extract blood samples on a regular basis. Because these infants are so small, it is not desirable to have to puncture the infant with a needle in order to extract blood or to give medicine.

In the past, right after the birth of the neonate, there is a ready available access opening into the bloodstream through the umbilical stump. Medical personnel take a small diameter catheter and insert such through the umbilical stump into the bloodstream. The precise position of this catheter is verified through the use of an x-ray. Once the correct position has been ascertained, it is necessary to tightly bind the catheter to the body of the neonate. Neonates move uncontrollably and thrash about. If the portion of the catheter that is located directly adjacent the umbilical stump is not tightly secured, the catheter will become dislodged. This dislodgement is most undesirable as it requires reinsertion which may be a most difficult thing to do since the umbilical stump tends to tightly close up a few days after birth.

In order avoid this dislodgement, in addition to suturing the catheter to the umbilical stump, nursing personnel have commonly used a securing bridge constructed from adhesive tape for the catheter. The bridge consists of bottom layers placed and adhesively secured against the stomach of the neonate around the umbilical stump. Upward extending sections are then attached to these bottom layers with separate layers being transversely applied to the upward extending layers with these transverse layers located in a facing abutting relationship and being adhesively secured together and binding therebetween the portion of the catheter that is located directly adjacent the umbilical stump. This installing procedure of such a bridge is time consuming and inherently costly since the salary of most nursing personnel is reasonably expensive. This tape created bridge takes several minutes for a nurse to construct. Also this bridge does not secure the catheter in the most secure manner. After the suturing, the bridge tape is then applied. These bridge tapes often lose adhesiveness permitting the catheter to become free from the bridge and dislodge from the neonate. Other factors contributing to dislodgement include poor taping, poor suturing, excessive movement of the neonate, loss of adhesiveness due to bodily secretions and procedures carried by nursing personnel such as weighing or moving of the infant. The suturing of catheters is a definite requirement. However, it is not adequate to totally rely on suturing but to also require taping of the catheter to insure that it will not be accidentally dislodged.

SUMMARY OF THE INVENTION

The catheter securing bridge of the present invention includes a thin sheet material base which has a bottom surface which includes an adhesive. This base includes a central opening which is of sufficient size so that the umbilical stump of the neonate can be located therewithin. The adhesive layer on the bottom of the base is to be normally covered by a release paper which is to be removed prior to installation. Pivotally mounted on the upper surface of the base are a pair of flaps. Prior to usage, these flaps are to be located in juxtaposition with the base with these flaps cooperating together to also form an opening of substantially equal size to the central opening. These flaps are capable of being moved to a usage position abutting each other with the abutting surfaces of the flaps also including an adhesive layer each of which is normally covered by a release paper. When the release papers are removed, the flaps are to be adhesively secured together binding therebetween a portion of the catheter that extends from the umbilical stump thereby securing the catheter in position preventing dislodgement from the umbilical stump.

The primary objective of the present invention is to construct a bridge which can be used on neonates to positively secure a catheter extending from the umbilical stump of the neonate preventing accidental dislodgement of the catheter.

Another objective of the present invention is to provide a catheter securing bridge which can be installed quickly and easily by nursing personnel in a minimum amount of time.

Another objective of the catheter securing bridge of the present invention is that the bridge can be constructed relatively inexpensively and therefore sold to hospitals for usage ion neonates at a relatively inexpensive price.

Another objective of the present invention is to construct the catheter securing bridge in an initial shape which facilitates conforming to the rounded configuration of the stomach of a neonate.

BRIEF DESCRIPTION OF THE DRAWING

FIG. 1 is an isometric view depicting initial installation of the catheter securing bridge of the present invention about the umbilical stump of a neonate;

FIG. 2 is an isometric view showing the catheter securing bridge of the present invention installed in position about the umbilical stump of a neonate and then showing its relation to a catheter that has been installed in the umbilical stump;

FIG. 3 is an isometric view depicting the removing of the release paper mounted on the flaps which are to be secured, together clamping the portion of the catheter that is located directly adjacent the umbilical stump in a tightly secured manner between the flaps;

FIG. 4 is an isometric view of the installed catheter securing bridge of the present invention;

FIG. 5 is a cross-sectional view taken along line 5—5 of FIG. 4; and

FIG. 6 is a cross-sectional view taken along line 6—6 of FIG. 4.

DETAILED DESCRIPTION OF THE SHOWN EMBODIMENT

Referring particularly to the drawing there is shown the catheter securing bridge 10 of this invention. The bridge 10 includes a sheet material base 12. Base 12 has a bottom surface which is coated with an adhesive layer 14. Adhesive layer 14 is normally covered prior to usage of the bridge 10 by a release paper 16. Release paper 16 is to be disengaged from the base 12 in the direction of arrow 18 as is shown in FIG. 1 when the bridge 10 is to be used. The base 12 can assume any desirable configuration with the primary shape of the base 12 being somewhat in the shape of a butterfly. This particular shape, with its gentle rounding curves, appears to be the easiest to apply the bridge 10 and also to remove the bridge 10. The base 12 includes a central opening 20. Extending laterally across the base 12 and diametrically across the opening 20 is a lateral axis 22.

Typical material of construction for the base 12 would be a fabric or plastic that is readily flexible. Clearly a desirable form of material is what is commonly used in conjunction with medical bandages which consist of a flexible mesh type of tape.

Integrally secured to the upper surface of the base 12 are a pair of flaps 24 and 26. The flaps 24 and 26 would normally be constructed of a transparent type of material with generally a plastic being preferred. Each of the flaps 24 and 26 are identical in shape with flap 24 including a semicircular opening 28 and flap 26 including a semicircular opening 30. Openings 28 and 30 are aligned when the flaps 24 and 26 are in juxtaposition with one another as is clearly shown in FIGS. 4 and 5 of the drawing. Openings 28 and 30 combine to form a single opening the same size as the central opening 20 when the flaps 24 and 26 are in the preuse position which is when the flaps 24 and 26 are in juxtaposition to the base 12. The inside surface of the flap 24 includes an adhesive layer 32. Similarly, the inside surface of the flap 26 includes an adhesive layer 34. Normally, the adhesive layer 32 is covered by a release paper 36 prior to usage of the bridge 10. In a similar manner, adhesive layer 34 is covered by a release paper 38 prior to usage of the bridge 10.

Prior to installing of the bridge 10, the bridge 10 is initially placed around the Umbilical stump 40 and against the skin 42 of the neonate. The bridge 10 is designed to be manufactured in four different sizes with size one designed to be used in conjunction with the smallest neonates, generally from seven hundred to twelve hundred grams, size two to be used in conjunction with twelve hundred to twenty two hundred gram neonates, size three to be used with between twenty two hundred and thirty eight hundred gram neonates, and size four from thirty eight hundred grams and up. Once the proper size of bridge 10 has been selected for the particular neonate, the catheter 44 is inserted through the central opening 20 and then inserted within the umbilical stump 40. The purpose of the catheter 44 is to provide direct vascular access to the neonate by way of the umbilical blood vessels. The catheter 44 has an outer end which terminates in a connector 46 which is to provide connection to intravenous feeding lines, syringes for the administration of medications, invasive monitoring of blood pressure and the withdrawal of blood for lab tests. The catheter 44 is placed in an artery or vein of the umbilicus by a neonatologist under sterile techniques. It is advanced a specific distance with placement of the tip 48 of the catheter 44 being verified by x-ray.

Once the catheter 44 is properly located and verified by x-ray and ready for infusion, the catheter 44 is then sutured in place on the umbilical stump 40. The installer then grasps the bridge 10, removes the release paper 16 and installs the bridge 10 on the skin 42 with the umbilical stump 40 centrally located within the central opening 20. The installer makes sure that the adhesive 14 assumes a secure bond with the skin 42. The wider top portion 50 of the base 12 is designed to face or be located closest toward the head of the neonate. To enhance the adhesion of the base 12 to the skin 42, it is important to make sure that the skin 42 around the umbilical stump 40 is clean and free of all antimicrobial agents such as Betadene (tradename). Cleaning is usually to be performed by warm soap and water. Alcohol is not to be used as it leaves a film on the skin 42.

The user then grasps one of the flaps such as flap 26 and removes the release paper 38. The user then grasps the catheter 44 and contorts such into a substantially u-shaped bend and place such against the adhesive 34 where the catheter 44 will now remain in this bent position. The user then removes the backing paper 36 and squeezes together the flaps 24 and 26 tightly securing therebetween the catheter 44.

Because the stomach of a neonate assumes a slightly rounded configuration, it is desirable that the basic shape of the bridge 10 in the area of the base 12 is to assume this similar rounded configuration. This rounded configuration is clearly shown in FIG. 6 where the bottom surface 52 of the base 12 is shown to be arcuate. The flaps 24 and 26 are designed so that their connections to the base 12 along the axis 22 are so as to accommodate this curvature of the base 12.

The bridge 10 of this invention can be used to secure more than one catheter 44 if more than one catheter is installed within a given umbilical stump 40. The bridge 10 completely surrounds the umbilical stump 40 and adhesively binds eight to ten centimeters of the indwelling catheter 44. The bridge 10 can be used for both an umbilical artery catheter and an umbilical venus catheter. The bridge 10 of this invention secures the catheter to the neonate to prevent dislodging thus preventing excessive bleeding and possible exsanguination.

What is claimed is:

1. A catheter securing bridge comprising:

a sheet material base having a bottom surface and an upper surface, a first adhesive layer cover said bottom surface, a central opening formed within said base, a lateral axis extending transversely across said base and diametrically across said central opening, said first adhesive layer adapted to be applied to the skin of a neonate with the umbilical stump located within said central opening;

a pair of sheet material flaps each having a lower edge, said lower edge of each said flap being secured to said base along said lateral axis, said flaps being pivotable relative to said base from a preuse position where said flaps are in juxtaposition with said base to be a usable position where said flaps are in juxtaposition with each other, each said flaps having an inside surface with said inside surfaces being joined together when said flaps are in said usable position, a second adhesive layer located on one of said inside surfaces, whereby a portion of the catheter is to be located between said inside surfaces and adhesively secured between said flaps when said flaps are in said usable position; and each said flap including a semicircular opening, each said semicircular opening connecting with said base at said lateral axis, when said flaps are in said preuse position said semicircular openings cooperate to form a single flap opening aligning with said central opening, whereby the catheter is first installed through said central opening and said flap opening prior to installation of the catheter with the umbilical stump of the neonate, whereby when said flaps are in said usable position there is space provided by said semicircular openings between said flaps and the umbilical stump which allow for slight movement by the neonate which does not affect the securement of said bridge.

2. The catheter securing bridge as defined in claim 1 wherein:
  said flap opening being approximately of the same size as said central opening when said flaps are in said preuse position.

3. The catheter securing bridge as defined in claim 1 wherein:
  said flaps being transparent.

4. The catheter-securing bridge as defined in claim 1 wherein:
  said bottom surface of said base constructed arcuate so as to conform to the stomach curvature of a neonate.

* * * * *